United States Patent [19]
Mileshkevich

[11] Patent Number: 5,948,929
[45] Date of Patent: Sep. 7, 1999

[54] FLUOROSILICON COMPOUNDS AND PREPARATION METHOD

[75] Inventor: Vladimir Mileshkevich, Bradwell, United Kingdom

[73] Assignee: FSO Limited, Sheffield, United Kingdom

[21] Appl. No.: 08/981,980

[22] PCT Filed: Jul. 10, 1996

[86] PCT No.: PCT/GB96/01644

§ 371 Date: Jan. 8, 1998

§ 102(e) Date: Jan. 8, 1998

[87] PCT Pub. No.: WO97/03078

PCT Pub. Date: Jan. 30, 1997

[30] Foreign Application Priority Data

Jul. 11, 1995 [GB] United Kingdom ................. 95141040

[51] Int. Cl.$^6$ ....................................................... C07F 7/08
[52] U.S. Cl. ........................................... 556/448; 252/573
[58] Field of Search ............................... 556/448; 252/573

[56] References Cited

U.S. PATENT DOCUMENTS 2,596,967  5/1952  Frost .
4,996,344  2/1991  Inomata et al. ........................ 556/448
5,262,557  11/1993  Kishita et al. ........................ 556/448

FOREIGN PATENT DOCUMENTS 802358  10/1958  United Kingdom .

OTHER PUBLICATIONS

"Reactions of Vinylsilanes With Tetrafluoroethylene", *Zhurnal Obshchei Khimii*, vol. 54, No. 10, 1984, pp. 2302–2306.

*Primary Examiner*—Paul F. Shaver
*Attorney, Agent, or Firm*—Trexler, Bushnell, Giangiorgi & Blackstone, Ltd.

[57] ABSTRACT

A fluorinated organosilicon compound is represented by formula (I).

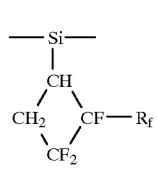

(I)

10 Claims, No Drawings

FLUOROSILICON COMPOUNDS AND PREPARATION METHOD

BACKGROUND OF THE INVENTION

1. Field of the Invention

This invention relates to fluorosilicon compounds and to a preparation method.

2. Description of the Prior Art

The majority of known fluorinated organosilicon compounds have structures in which a fluorine-containing groups such as perfluoroalkyl is bonded to a silicon atom through a dimethylene or trimethylene group. Synthesis of these compounds usually requires many stages, including a Grignard reaction and a reaction involving a precious metal catalyst, such as platinum (cf. U.S. Pat. No. 5,202,453; EP 0,538,061 A2). Reactions for making fluorinated organosilicon compounds by way of a cyclization process between olefine derivatives of silicone and fluorine have also been described (cf. U.S. Pat. No. 2,596,967; UKP 760,201 and 802,358; Holbrook G. W. J. Am.Chem.Soc 82 825 (1960); Park J. D. J. Org.Chem., 25, 1628 (1960). However, this reaction has been largely ignored over the past ten years.

SUMMARY OF THE INVENTION

According to the first aspect of the invention there is provided a fluorinated organosilicon compound represented by the formula:

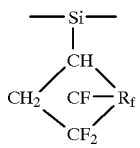

Preferably the compound is represented by the following formula:

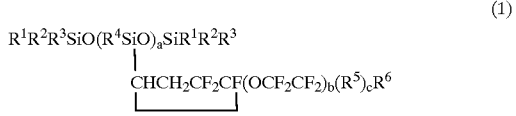
(1)

wherein $R^1$, $R^2$, $R^3$ and $R^4$ are independently selected from alkyl groups having 1–4 carbon atoms or independently selected from the above alkyl groups, the $CF_3CH_2CH_2$— group, and the $R^6(R^5)_c(CF_2CF_2O)_bCFCF_2$ $CH_2CH$ — group, where $R^6$, $R^5$, a,b and c are as hereinafter defined. $R^5$ is a bivalent group such as —$OCF_2$—, —$OCF_2CF_2$,— or —$OCF_2CF(CF_3)$—. $R^6$ is a —$OCF_3$— group or —F atom. a is an integer from 0 to 6, b is zero or 1, c is an integer between 2 and 6.

Fluorinated organosilicon compounds in accordance with the invention have a wide operating temperature range and excellent chemical resistance; they are oil- and water- repellent and have outstanding dielectric properties. In addition, due to the phenomenon of "super-flexibility", the viscosity of these materials is much lower than their molecular weight would suggest. All these properties, together with their density, which can be arranged to be in the range 1.3–1.7 g/ml make these liquids very suitable for use as base liquids in Electro-Rheological (ER) Fluids as well as more general applications.

The invention includes a cyclo butane ring of formula:

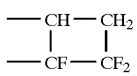

A preferrred formula being:

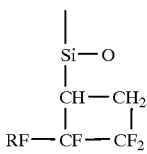

According to a second aspect of the invention, there is provided a method of manufacturing a compound in accordance with the first aspect by reacting a vinyl siloxane of general formula:

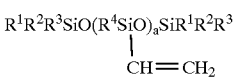

wherein $R^1$, $R^2$, $R^3$,and $R^4$ have the meanings defined above, with a perfluoro-olefin of the general formula:

wherein $R^5$, $R^6$, b and c are as previously defined above, in the present of a free radical inhibitor.

The compounds are produced by a reaction between vinyl siloxane and perfluoro-olefin in the presence of a free radical inhibitor at elevated temperature and pressure.

Preferably, in the cyclization reaction of the vinylsiloxane and the perfluoro-olefin, the ratio of reactants is in the range 1-2 moles of perfluoro-olefin for each mole of vinyl siloxane, preferably between 1.1 and 1.6. The reaction temperature may be in the range 150–250° C. and preferably between 180 and 230° C. The reaction time may be 5–100 hours, and typically between 10 and 70 hours. The reaction is preferably carried out at elevated pressure in an autoclave.

Typical examples of fluorinated organosilicon compounds prepared by this method include:

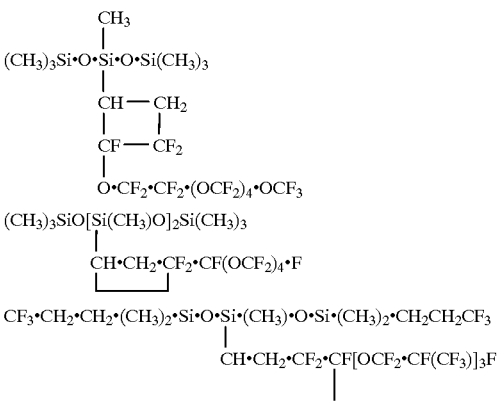

I claim:

1. Fluorinated organosilcon compounds having at least one cyclobutane ring connected with fluoro contained groups through oxygen atom, the compounds being represented by the formula

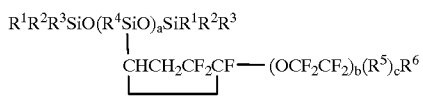

5 wherein $R^1$, $R^2$, $R^3$, and $R^4$ are independently selected from alkyl groups having 1–4 carbon atoms, the $CF_3CH_2CH_2$— group, the $CH_2$=$CH$— and the

15

$R^5$ is a bivalent group selected from —$OCF_2$—, —$OCF_2CF_2$—, —$OCF_2CF(CF_3)$—, $R^6$ is a $CF_3O$— group or a $C_3F_7O$— group attached to the terminated carbon atom of the $R^5$ group, a is an integer from 0 to 6, b is zero or 1, c is an integer between 1 and 6.

2. A compound as claimed in claim 1, having the formula:

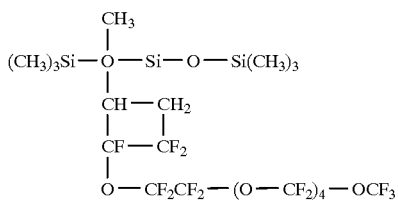

3. A compound as claimed in claim 1 having the formula:

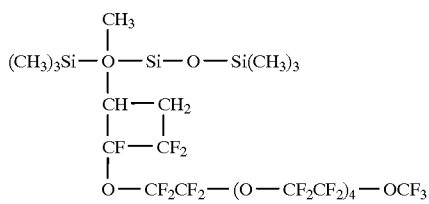

4. A compound as claimed in claim 1 having the formula:

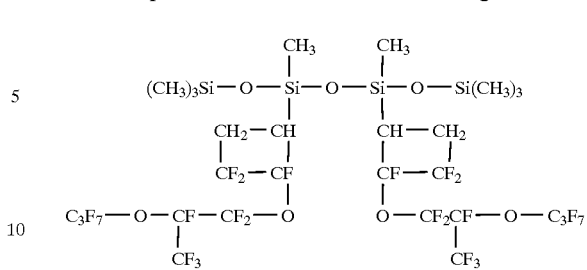

5. A method of manufacturing a compound as defined in any one of claims 1 to 4 by reacting a vinyl siloxane of general formula

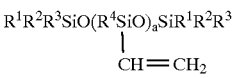

wherein $R^1$, $R^2$, $R^3$, $R^4$ and a are as defined in claim 1, with a perfluoro-olefin of general formula:

wherein $R^5$, $R^6$, b and c are as defined in claim 1, in the presence of a free radical inhibitor.

6. A method as claimed in claim 5, wherein the ratio of reactants is in the range 1N to 2N moles of perfluoro-olefin for each mole of vinyl siloxane, preferably between 1.1 N and 1.6N, where N is the number of vinyl groups on a single molecule of the vinyl siloxane.

7. A method as claimed in claim 5, wherein the reaction is carried out at a temperature range 120–250° C. and preferably between 150 and 200° C.

8. A method as claimed in any one of claim 5, wherein the reaction is carried out over the time period of 5–100 hours, and preferably between 10 and 70 hours.

9. A method as claimed in any one of claim 5, wherein the reaction is carried out at elevated pressure.

10. An electro-rheological fluid having as its base liquid a compound as defined in any one of claims 1 to 4, or a mixture of such compound with other fluorine-containing compounds.

* * * * *